(12) United States Patent
Li et al.

(10) Patent No.: US 11,491,488 B2
(45) Date of Patent: Nov. 8, 2022

(54) SPERM SORTING CHIP AND METHOD FOR SORTING SPERM USING THE SAME

(71) Applicant: NATIONAL YANG MING CHIAO TUNG UNIVERSITY, Hsinchu (TW)

(72) Inventors: Bor-Ran Li, Hsinchu (TW); Chung-Hsien Huang, Tainan (TW)

(73) Assignee: iPreg Inc., Taipei (TW)

( * ) Notice: Subject to any disclaimer, the term of this patent is extended or adjusted under 35 U.S.C. 154(b) by 355 days.

(21) Appl. No.: 16/881,099

(22) Filed: May 22, 2020

(65) Prior Publication Data

US 2020/0368748 A1 Nov. 26, 2020

(30) Foreign Application Priority Data

May 23, 2019 (TW) .................................. 108117772

(51) Int. Cl.
*B01L 3/00* (2006.01)
*C12M 3/06* (2006.01)
(Continued)

(52) U.S. Cl.
CPC ....... *B01L 3/502761* (2013.01); *C12M 23/16* (2013.01); *C12M 47/04* (2013.01);
(Continued)

(58) Field of Classification Search
CPC ....... B01L 3/502761; B01L 2200/0652; B01L 2300/0861; C12M 23/16; C12N 5/0081
See application file for complete search history.

(56) References Cited

U.S. PATENT DOCUMENTS

| 2006/0270021 A1* | 11/2006 | Takayama ........... B01L 3/50273 435/283.1 |
| 2010/0291535 A1 | 11/2010 | Yao |
| 2018/0119087 A1* | 5/2018 | Lam ...................... C12M 47/04 |

FOREIGN PATENT DOCUMENTS

TW  201040524 A1  11/2010

OTHER PUBLICATIONS

Wu et al., "High-throughput flowing upstream sperm sorting in a retarding flow field for human semen analysis", Analyst, 2017, vol. 142, pp. 938-944.

(Continued)

*Primary Examiner* — Michael McCullough
*Assistant Examiner* — Jessica L Burkman
(74) *Attorney, Agent, or Firm* — Fei-hung Yang (57) ABSTRACT

The present invention provides a sperm sorting chip and a method for sorting sperm using the same. Said sperm sorting chip includes: a flow channel structure sequentially configured with a gradually diverging flow field region, a main flow channel, and a gradually converging main flow channel intercommunicated with each other from a first side end to a second side end; a fluid injection port, a semen injection port, and a semen extraction port separately located at the first side end and communicated with a main input channel of the gradual diverging flow field region; and a waste fluid outlet located at the second side end and communicated with the gradually converging main flow channel. The gradually diverging flow field region further includes a plurality of sub-input channels derived from the main input channel and converged into the main flow channel, and the plurality of sub-input channels have a gradually widening channel width at the junction with the main flow channel. By contrast, the gradually converging main flow channel has a gradually narrowing channel width toward the waste fluid outlet.

11 Claims, 7 Drawing Sheets

(51) Int. Cl.
*C12M 1/00* (2006.01)
*C12N 5/076* (2010.01)
*C12N 5/00* (2006.01)

(52) U.S. Cl.
CPC ........... *C12N 5/0081* (2013.01); *C12N 5/061* (2013.01); *B01L 2200/0652* (2013.01); *B01L 2300/0861* (2013.01); *B01L 2300/0864* (2013.01)

(56) References Cited

OTHER PUBLICATIONS

Zaferani et al., "Rheotaxis-based separation of sperm with progressive motility using a microfluidic corral system", PNAS, Aug. 14, 2018, vol. 115, No. 33, pp. 8272-8277.

* cited by examiner

SPERM SORTING CHIP AND METHOD FOR SORTING SPERM USING THE SAME

BACKGROUND OF THE INVENTION

1. Field of the Invention

The present disclosure relates to a sperm sorting chip and a method for sorting sperm using the same. In particular, the present disclosure relates to a sperm sorting chip comprising a waste fluid outlet and a semen extraction port which are separated from each other and a method for sorting sperm using the same.

2. Description of the Prior Art

The poor quality of males' sperm is often one of the main reasons of infertility, and, thus, among the technologies of artificial fertilization, the technology of sorting sperm attracts more and more attention. Therefore, even though the quality of sperm may mainly be determined by morphology, however, sperm are easily injured after morphology detection using technologies such as dyeing, and hence these technologies are not suitable to be used to assist reproduction. Therefore, in general, sperm for artificial fertilization are detected and screened via sperm kinematics which will not injure sperm.

Currently many technologies for sorting sperm using sperm kinematics and corresponding microfluidic chips have been developed. However, in order to increase the opportunities for fecundation and improve the quality of fertilized eggs, it is still essential to enhance technologies for sorting sperm and to design microfluid chips which can separate out sperm of good quality more quickly.

SUMMARY OF THE INVENTION

A Method for Solving the Problem

In order to solve the aforementioned problems, an embodiment of the present disclosure provides a sperm sorting chip comprising: a flow channel structure sequentially configured with a diverging flow field region, a main flow channel, and a converging main flow channel intercommunicated with each other from a first side end to a second side end; a fluid injection port, a semen injection port, and a semen extraction port, separately located at the first side end and communicated with a main input channel of the diverging flow field region: and a waste fluid outlet located at the second side end and communicated with the converging main flow channel. Wherein, the diverging flow field region further includes a plurality of sub-input channels derived from the main input channel and converged to the main flow channel, and a plurality of sub-input channels have a gradually widening channel width at the junction with the main flow channel. In addition, the converging main flow channel has a gradually narrowing channel width toward the waste fluid outlet.

According to another embodiment of the present disclosure, a method for sorting sperm using the sperm sorting chip includes: a step (a): injecting a fluid through the fluid injection port, and making the fluid enter the flow channel structure continuously to establish a preset flow field; a step (b): injecting a predetermined amount of semen to the main input channel through the semen injection port; a step (c): waiting a predetermined amount of time for the semen to be screened by the preset flow field and a step (d): applying an external extraction force through the semen extraction port to extract the screened semen. Wherein, relatively inactive sperm in the semen are transported to the waste fluid outlet by the preset flow field, and the screened semen includes relatively active sperm in the semen.

Results Compared to the Prior Art

According to a sperm sorting chip and a method for sorting sperm provided by each embodiment of the present disclosure, it is possible to extract sperm that die and collect required sperm by using the waste fluid outlet and the semen extraction port located at opposite two side ends respectively. Therefore, the problem of having mixed sperm with different qualities when extracting waste fluid from the same port as the port for collecting sperm will be decreased or avoided so as to enhance the quality of collected sperm.

DETAILED DESCRIPTION OF THE PREFERRED EMBODIMENT

Various embodiments are described in the following sentences, and people skilled in the art can easily understand the conception principles of the present disclosure with reference to descriptions and FIGs. However, even though some specific embodiments are described in the specification in detail, these embodiments merely represent examples, without any intention to limit or exhaust various aspects. Therefore, it is easy for people skilled in the art to understand and complete various alternations and modifications of the present disclosure without departing from the conception principles of the present disclosure.

Figure 1:
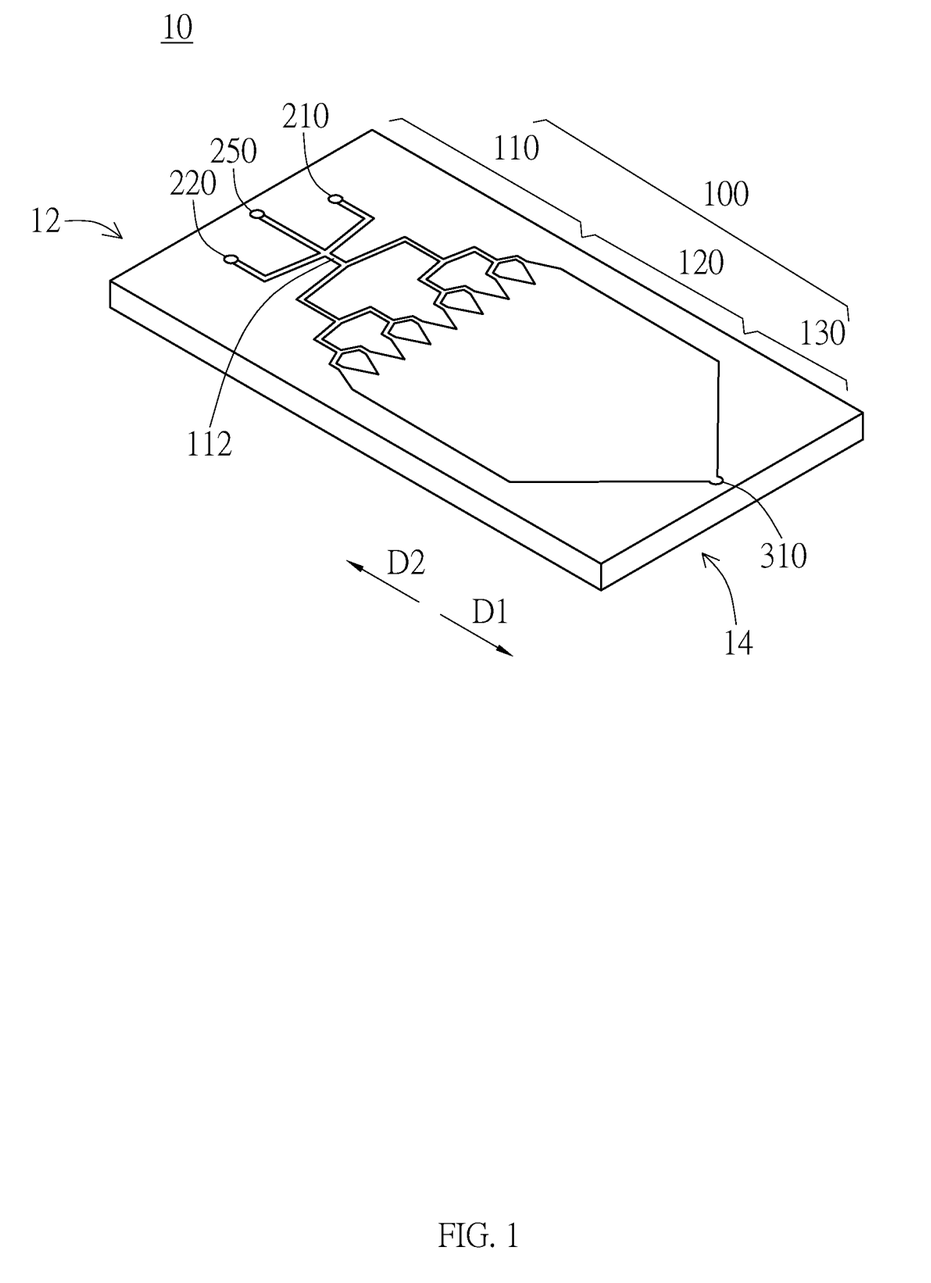
FIG. 1 is a diagram of a sperm sorting chip in an embodiment of the present disclosure.

Please refer to FIG. 1 illustrating an embodiment of the present disclosure. A sperm sorting chip 10 includes a flow channel structure 100 and a fluid injection port 210, a semen injection port 220, a semen extraction port 250, and a waste fluid outlet 310 intercommunicated with the flow channel structure 100. In particular, the flow channel structure 100 of the sperm sorting chip 10 extends from a first side end 12 to a second side end 14, and is sequentially configured with a diverging flow field region 110, a main flow channel 120, and a converging main flow channel 130 intercommunicated with each other. Wherein, the fluid injection port 210, the semen injection port 220, and the semen extraction port 250 are separately located at the first side end 12, and communicated with the main input channel 112 of the diverging flow field region 110. In particular, please refer to FIG. 2A with FIG. 1, the fluid injection port 210, the semen injection port 220, and the semen extraction port 250 are located at the first side end 12 of the flow channel structure 100 and separated from each other, and they are communicated with the main input channel 112 of the diverging flow field region 110 respectively through connecting ducts 210t, 220t, and 250t. As mentioned above, through these structure, fluids or semen input from the fluid injection port 210 or the semen injection port 220 may flow to the main input channel 112 of the diverging flow field region 110 and enter the flow channel structure 100 subsequently. On the other hand, fluid or semen in the flow channel structure 100 may also be extracted by the semen extraction port 250 through the main input channel 112.

Figure 2A:
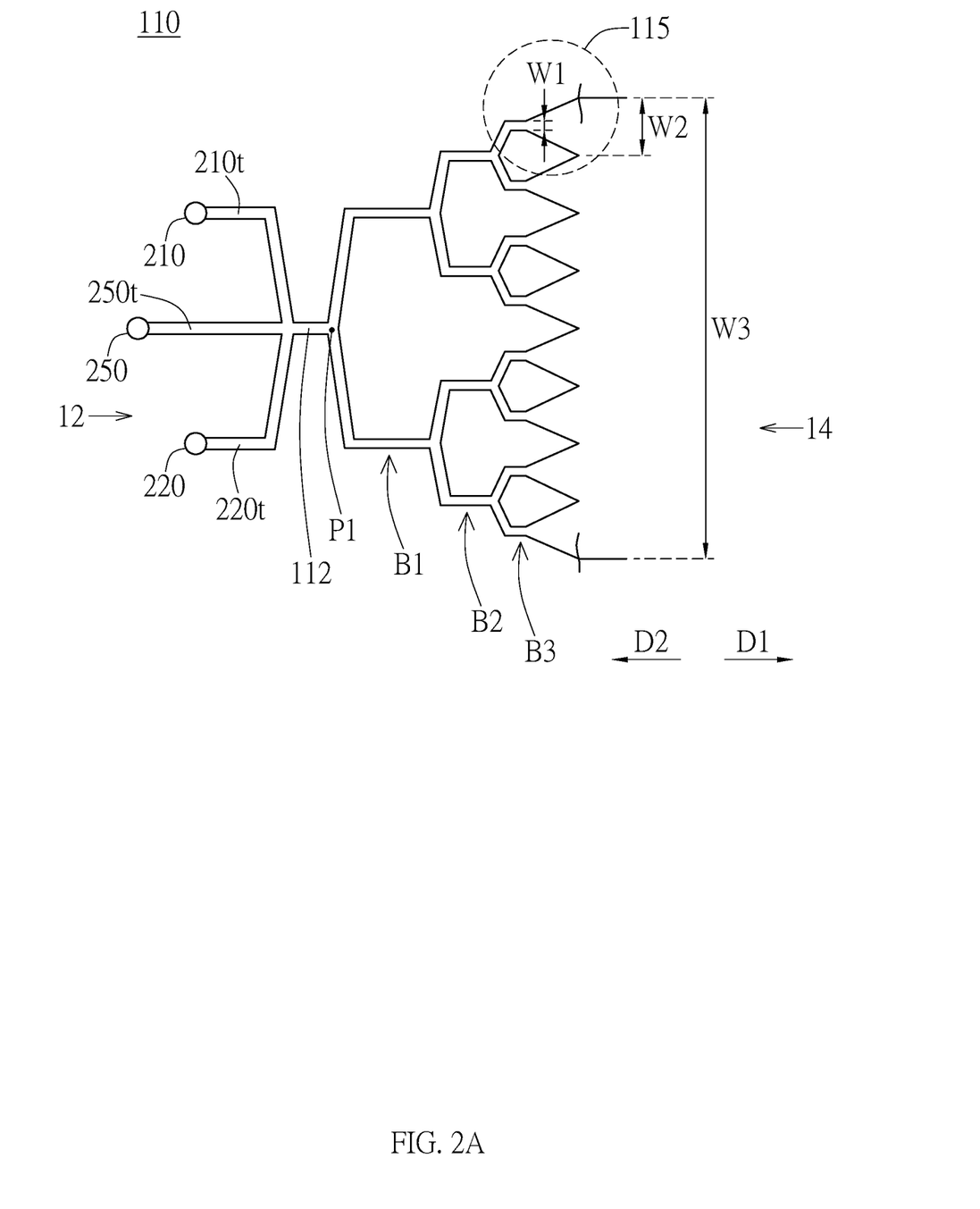
FIG. 2A is an enlarged diagram of a diverging flow field region in an embodiment of the present disclosure.

Then, please continue to refer to FIG. 1, and FIG. 2A. The diverging flow field region 110 further includes a plurality of sub-input channels 115 derived from the main input channel 112 and converging to the main flow channel 120. For example, eight sub-input channels 115 are illustrated in FIG. 1 and FIG. 2A. However, the number of sub-input channels 115 illustrated here is merely an example, and the present disclosure is not limited thereto. Wherein, the plurality of sub-input channels 115 may have a gradually diverging channel width at the junction with the main flow channel 120 by various ways. For example, the junctions between each of the plurality of sub-input channels 115 and the main flow channel 120 may be triangle shaped as illustrated in FIG. 1 and FIG. 2A (wherein the bases correspond to the boundaries between the sub-input channels 115 and the main flow channel 120) and may gradually widen from a channel width W1 to a channel width W2 when entering the main flow channel 120 (wherein lengths of bases may correspond to the channel width W2; however, the present disclosure is not limited thereto). Thus, when fluid is transported here, a predetermined sub-flow field in which flow velocities are slowed down may be established here (the boundaries between each of the plurality of sub-input channels 115 and the main flow channel 120) by increasing sectional areas that the fluid pass through. In particular, the flow velocity of the flow field may be determined by V=Q/A, wherein V is the flow velocity, Q is the volume of the a microfluid (mainly, a fluid including semen), and A is the sectional area of the flow channel. Thus, in the general situation where the height of the microfluid chip's flow channel is fixed (In the following paragraphs, the heights of the flow channels of the flow channel structure 100 are assumed to be the same), the flow velocity decreases as the channel width increases. Based on this principle, sub flow fields with different flow velocities may be established at different areas of the flow channel structure 100 so as to sort sperms with different mobilities.

According to some embodiments of the present disclosure (please refer to FIG. 2A), in the diverging flow field region 110, a tree structure is formed starting at the node P1 (located at the end of the main input channel 112 away from the first side end 12) toward the second side end 14. For example, in some embodiments, a plurality of sub-input channels 115 may form a tree structure based on the starting node P1. In addition, according to other embodiments, as illustrated in FIG. 1 and FIG. 2A, a plurality of sub-input channels 115 may also form one or more tiers of tree structure sub-channels from the starting node P. In particular, the tree structure may firstly branch out to form two sub-channels (first tier branches B1) based on the starting node P1, and each of the two sub-channels in the first tier branches B1 may respectively branch out to form two sub-channels (second tier branches B2), and each of the four sub-channels of the second tier branches B2 may respectively form two sub-channels (the third tier branches B3) again. In other words, as shown in the embodiments illustrated in FIG. 1 and FIG. 2A, there may be two tiers of branches (the first tier branches B1 and the second tier branches B2) between a plurality of sub-input channels 115 and the starting node P1, and the plurality of sub-input channels 115 are the third tier branches B3 based on the starting node P1. However, the number of the plurality of sub-input channels 115, the number of tiers of tree structure sub-channels between the plurality of sub-input channels 115 and the starting node P1, the number of sub-channels branching out from a channel branch are not limited to the illustrated embodiments of the present disclosure.

Since a plurality of sub-input channels 115 converge into a main flow channel 120 by widening their channel widths (from the channel width W1 to the channel width W2), therefore, in some embodiments, the sum of the largest widths of each of the plurality of sub-input channels 115 (for example, the second channel width W2) may be smaller than or equal to the channel width W3 of the main flow channel 120.

Figure 2B:
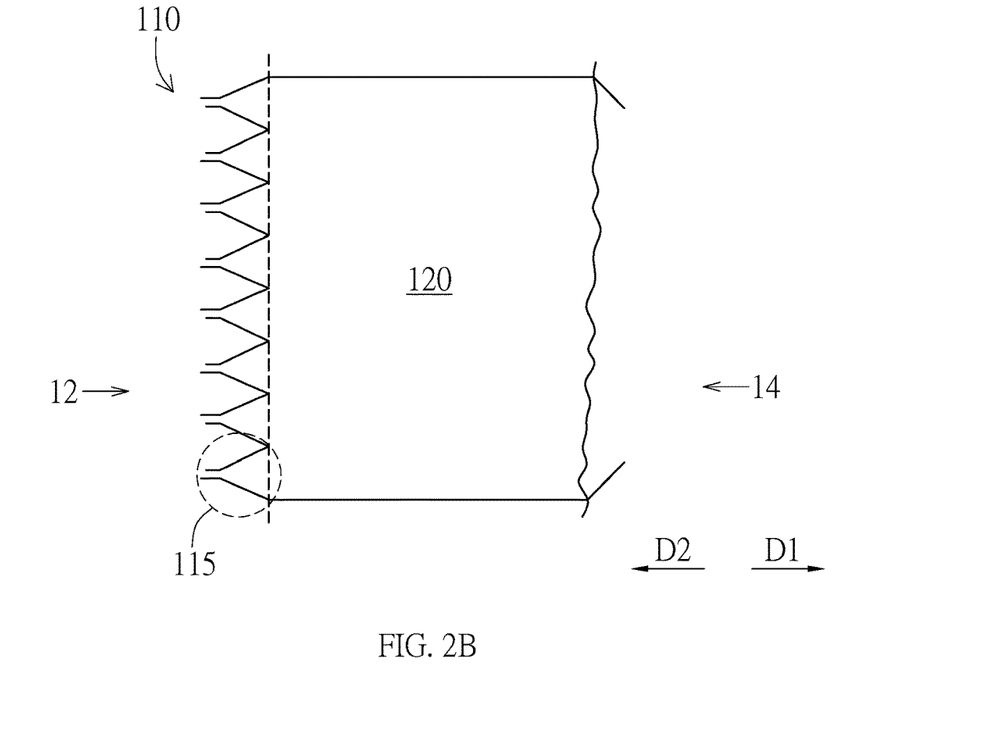
FIG. 2B is an enlarged diagram of a main flow channel 120 in an embodiment of the present disclosure.

Please refer to FIG. 1 and FIG. 2B. As mentioned above, the main flow channel 120 comes after the diverging flow field region 110, and fluid, semen or a combination thereof may be slowed down by a guide of the diverging flow field region 110 and converged to the main flow channel 120. According to a preferred embodiment, the main flow channel 120 has a fixed channel width, and thus fluid converged into the main flow channel 120 after slowing down may keep approximately a fixed flow velocity in the main flow channel 120. Therefore, semen guided to enter the main flow channel 120 may be screened in the main flow channel 120. The process will be described in detail in the following paragraphs.

Figure 2C:
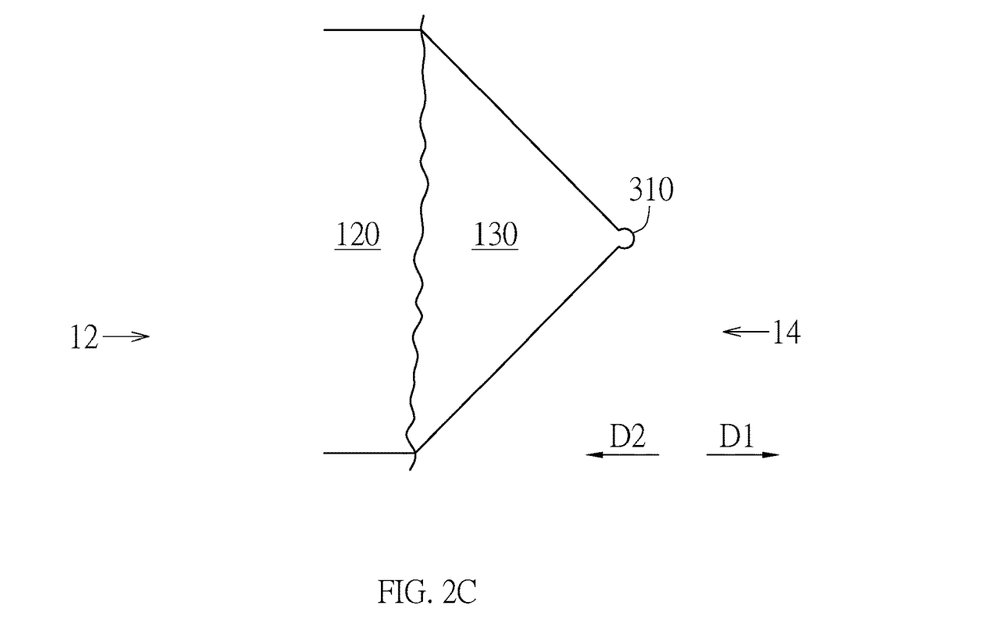
FIG. 2C is an enlarged diagram of a converging main flow channel in an embodiment of the present disclosure.

Please refer to FIG. 1 and FIG. 2C, the main flow channel 120 extending from the side facing the first side end 12 to the side facing the second side end 14 is subsequently connected to the converging main flow channel 130 at the end portion. The converging main flow channel 130 has a gradually narrowing channel width toward the waste fluid outlet 310 located at the second side end 14. For example, the converging main flow channel 130 may gradually converge into the waste fluid outlet 310. As shown in FIG. 1 and FIG. 2C, the converging main flow channel 130 may form a triangle-like shape, and the top of the triangle is located at the waste fluid outlet 310. However, it merely represents an example, and the ways to converge and the types of the converging main flow channel 130 are not limited to the embodiments illustrated here.

Through the aforementioned structure, the preset sub-flow field for speed up may be established in the converging main flow channel 130 by decreasing the cross-section area for fluids to pass through, and such structure may facilitate the transport of the waste fluid to be removed (including sperm that are eliminated) to the waste fluid outlet 310 communicated with the converging main flow channel 130.

In order to construct the flow channel structure 100, any material suitable to be used in microfluid chips or biological detection devices may be used for the structure of the flow channel structure 100. For example, according to some embodiments of the present disclosure, glass, quartz, polymethyl methacrylate, polydimethylsiloxane (PDMS) and the like may be used, and the present disclosure is not limited thereto. In addition, according to some embodiments of the present disclosure, composite materials may be used as materials for constructing the flow channel structure 100, or one could form each part using a different material and combine the parts. For example, it is possible to construct a molded channel structure and attach it to a slide so as to form the sperm sorting chip 10.

According to some embodiments, the channel height of the flow channel structure 100 may be fixed at 100 µm; however, the present disclosure is not limited thereto.

According to some embodiments of the present disclosure, it is possible to further connect a syringe pump to one or more of the fluid injection port 210, the semen injection port 220, the semen extraction port 250, and the waste fluid outlet 310. In addition, according to some other embodiments of the present disclosure, it is possible to further connect a duct to the fluid injection port 210, the semen injection port 220, the semen extraction port 250, and the waste fluid outlet 310 so as to help the input of fluids or semen from the outside, or to help the output of fluids or semen to the outside. Furthermore, to decrease or avoid the likelihood of inputting or outputting specific fluids or semen from ports other than the pre-designated ports, according to other embodiments of the present disclosure, one or more of the fluid injection port 210, the semen injection port 220, the semen extraction port 250, or the waste fluid outlet 310 may be selectively opened or closed. For example, one or more of the fluid injection port 210, the semen injection port 220, the semen extraction port 250, and the waste fluid outlet 310 may have gates that can be selectively opened or closed, and may be closed or opened when required. However, this is merely an example, and the designs of one or more of the fluid injection port 210, the semen injection port 220, the semen extraction port 250, and the waste fluid outlet 310 being able to be selectively opened or closed are not limited thereto.

In the aforementioned paragraphs and FIG. 1 to FIG. 2C, the fluid injection port 210, the semen injection port 220, the semen extraction port 250, and the waste fluid outlet 310 are essentially configured so that the fluid injection port 210, the semen injection port 220, and the semen extraction port 250 are located at the first side end 12 of the flow channel structure 100, and the waste fluid outlet 310 is located at the second side end 14 of the flow channel structure 100. Thus, locations of the fluid injection port 210, the semen injection port 220 and the semen extraction port 250 located at the first side end 12 may be adjusted correspondingly when required. For example, even though all of the fluid injection port 210, the semen injection port 220, and the semen extraction port 250 are located at the first side end 12 of the flow channel structure 100, they are configured to be separated from each other, and each may keep a different distance or the same distance from the main flow channel 120 along the downstream direction D1 from the first side end 12 toward the second side end 14. In addition, even though the semen extraction port 250 is located at the center of the first side end 12 of the flow channel structure 100, the fluid injection port 210 is located at the left side of the first side end 12 of the flow channel structure 100, and the semen injection port 220 is at the right side of the first side end 12 of the flow channel structure 100 along the downstream direction D1 from the first side end 12 toward the second side end 14 as illustrate in FIG. 1 and FIG. 2A, it merely represents an example and the present disclosure is not limited thereto. For example, the semen extraction port 250 may also be located at the center of the first side end 12 of the flow channel structure 100, the fluid injection port 210 may also be located at the right side of the first side end 12 of the flow channel structure 100, and the semen injection port 220 may also be located at the left side of the first side end 12 of the flow channel structure 100 along the downstream direction D1 from the first side end 12 toward the second side end 14. Furthermore, the semen extraction port 250 may be located at the right side of the first side end 12 of the flow channel structure 100, the fluid injection port 210 may be located at the left side of the first side end 12 of the flow channel structure 100, and the semen injection port 220 may be located at another location such as the center of the first side end 12 of the flow channel structure 100 along the downstream direction D1 from the first side end 12 toward the second side end 14.

According to a preferred embodiment of the present disclosure, the fluid injection port 210 for injecting fluids is located at a relatively high location in the direction of gravity with respect to the diverging flow field region 110, the main flow channel 120, the converging main flow channel 130 or a combination thereof. For example, the fluid injection port 210 may be designed to be essentially located at a higher location than the diverging flow field region 110, the main flow channel 120, the converging main flow channel 130 or a combination thereof in the whole flow channel structure 100. Through the design, the flow velocity of fluids may be kept stable continuously by merely using gravity when injecting fluids through the fluid injection port 210. Therefore, the preset flow field with approximately fixed flow velocity may be established in the whole flow channel structure 100 by gravity. However, the above is merely an example, and the fluid injection port 210 may make fluids pass through and keep the preset flow field at the required flow velocity by other means or structures.

In the following paragraphs, a method for sorting sperm 20 using the sperm sorting chip 10 illustrated in FIG. 1 according to an embodiment of the present disclosure is described with reference to FIG. 3 to FIG. 4D.

Figure 3:
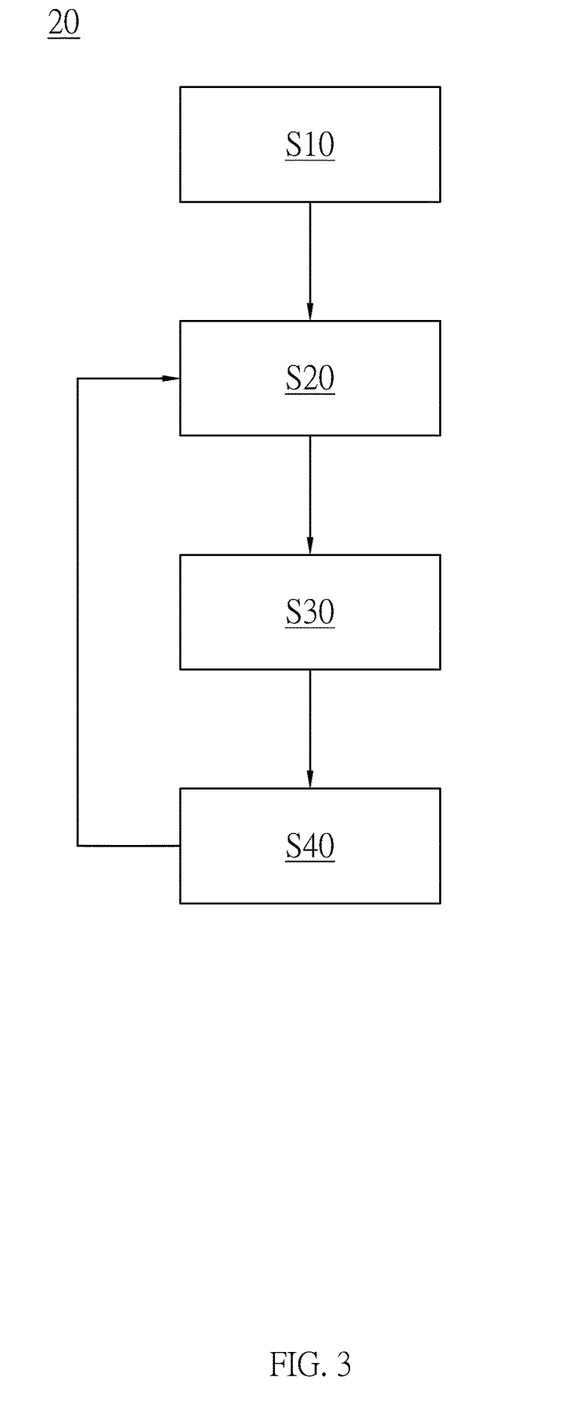
FIG. 3 is a flowchart of a method for sorting sperm using the sperm sorting chip in an embodiment of the present disclosure.

Firstly, please refer to FIG. 3. According to an embodiment of the present disclosure, the method for sorting sperm 20 using the sperm sorting chip 10 comprises: a step S10 of establishing a preset flow field, a step S20 of injecting semen 50, a step S30 of waiting for the semen to be screened, and a step S40 of extracting screened semen 60. In particular, in the step S10 (please refer to FIG. 4A together with FIG. 3), a fluid 40 may be injected through the fluid injection port 210 of the sperm sorting chip 10, and the flow channel structure 100 is preferably filled with the fluid 40. Here, the fluid 40 may be any sperm culture media or buffer media which doesn't injure sperm at least. In particular, the fluid 40 is used for establishing a preset flow field F0 in the flow channel structure 100, so as to sort the sperm using the preset flow field F0. Therefore, the fluid 40 should be flowable so as to establish the flow field of the required flow velocity and a sperm culture media to make sperms survive or swim, or should at least be a fluid which doesn't injure sperm or has low level of harm to sperm. For example, the fluid 40 may be a modified human tubal fluid (mHTF); however, the present disclosure is not limited thereto.

Figure 4A:
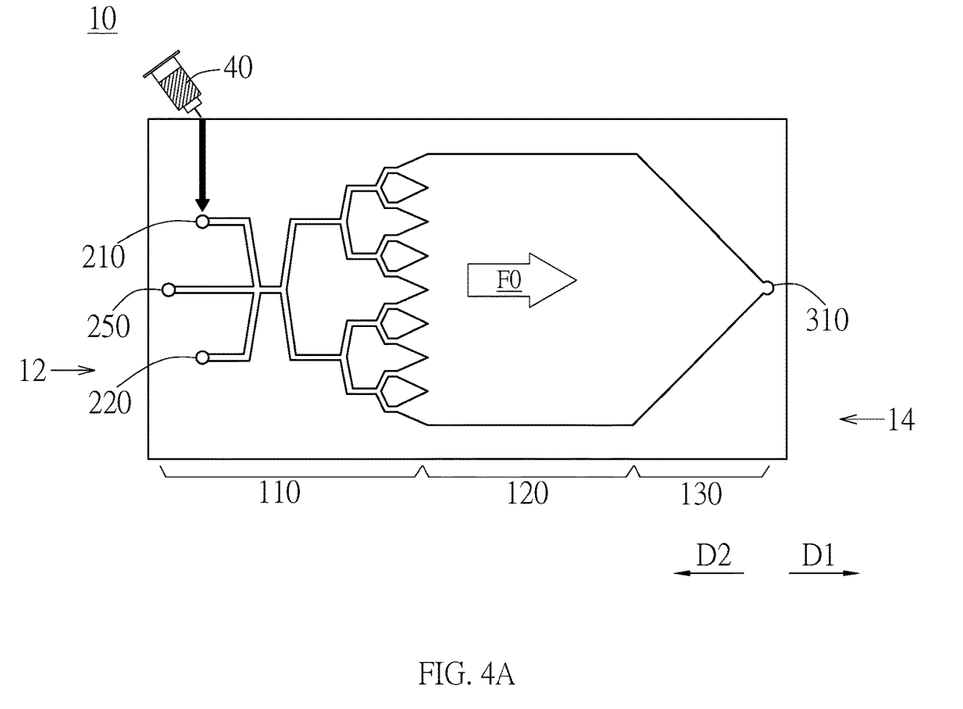
FIG. 4A to FIG. 4D are diagrams of operating each step of the method in an embodiment of the present disclosure, respectively.

As mentioned above, in the step S10, the fluid 40 is injected through the fluid injection port 210 so as to establish the preset flow field F0, and the preset flow field F0 is kept in the following steps. That is, after injecting in the fluid 40 in the step S10, it is essential to keep the fluid 40 going through the flow channel structure 100. Therefore, the whole space of the flow channel structure 100 (the diverging flow field region 110, the main flow channel 120, and the converging main flow channel 130) may be filled with the fluid 40, and the fluid 40 may establish the preset flow field F0 in which the flow velocity is approximately fixed in the whole flow channel structure 100 due to the fluid 40 going through continuously.

Figure 4B:
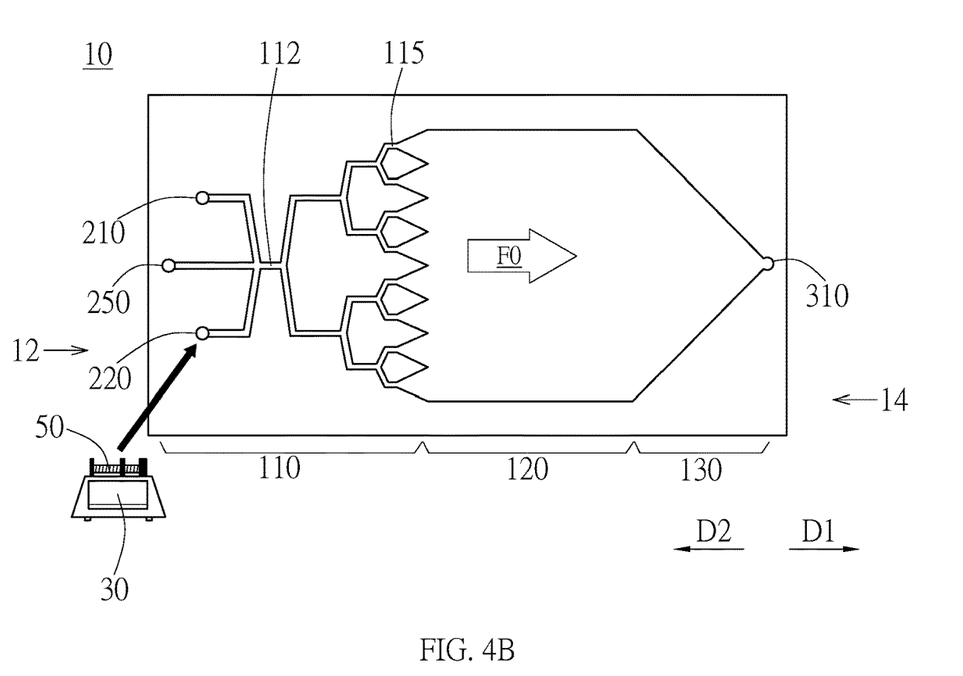

Next, please refer to FIG. 4B together with FIG. 3. The step S20 of injecting the semen 50 is conducted after the step S10 is completed. In particular, a predetermined amount of the semen 50 may be injected into the diverging flow field region 110 through the semen injection port 220 of the sperm sorting chip 10 in the step S20. For example, the predetermined amount of the semen 50 may be injected by using a syringe pump 30 but not limited thereto. In particular, the predetermined amount of the semen 50 may be injected into the main input channel 112 of the diverging flow field region 110 so as to make the semen 50 and the fluid 40 converge. Thus, the predetermined amount of the semen 50 may be guided by the preset flow field F0 established by the fluid 40 to flow along the downstream direction D1 from the first side end 12 toward the second side end 14.

Thus, the aforementioned semen 50 may be guided by the preset flow field F0 to flow to the plurality of sub-input channels 115 along the downstream direction D1 in the main input channel 112, and thus might be guided to flow from the diverging flow field region 110 to the main flow channel 120.

According to some embodiments, as opposed to a single sub-input channel, when sperm are guided by a plurality of sub-input channels 115 to be communicated to the main flow channel 120, the distribution of the sperm when they are first guided are more uniform across the junctions of the plurality of sub-input channels 115 and the main flow channel 120 or in the main flow channel 120. In addition, when the smaller channel width is widened into the larger channel width, the guided sperm may be distributed from the end of the sub-input channel to form a sector. And, through the sectors formed by each of the plurality of sub-input channels 115, it is possible to make all of the sperm distributed to form a shape close to a wavy line or a straight line, which further decreases the trend of the non-uniform distance between the sperm and the end of the sub-input channel at first due to the dispersions forming sectors. Furthermore, in following paragraphs, it will be described that in the process of sorting and collecting, the design of a plurality of sub-input channels 115 can decrease the extent of channel width narrowing when going countercurrent, and in turn decreases the level of difficulty for the sperm to swim back, which makes it possible to collect more sperm which swim back to the end of the sub-input channel 115. However, the above are merely examples. In some embodiments of the present disclosure, depending on the requirements for sperm collection, it is also possible to only use one single sub-input channel 115 with widening channel width to communicate with the main flow channel 120.

Figure 4C:
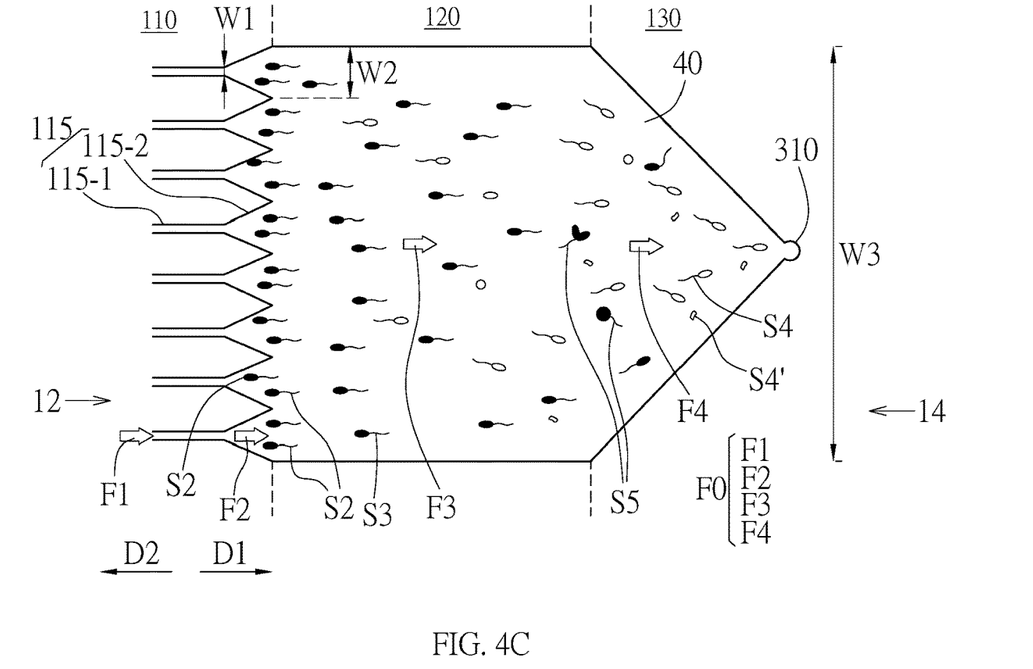
Figure 4D:
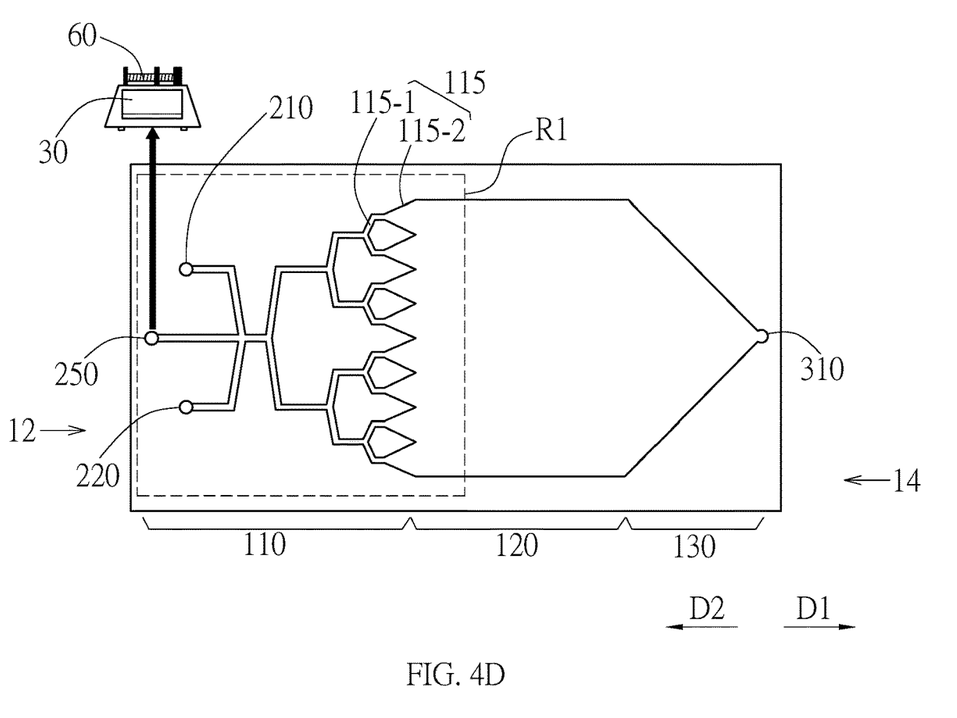

Next, please refer to FIG. 4C together with FIG. 3. After completing the step S20, one can conduct the step S30 of waiting for sorting. That is, it is possible to wait a predetermined amount of time for semen 50 to be screened by the preset flow field F0. In particular, since sperm have the ability to swim back in the slow flow field, it is possible to sort out sperm having better qualities by using the preset flow field F0 after the semen 50 is guided to enter the flow channel structure 100.

In particular, the preset flow field F0 may have sub flow fields in different locations based on the properties of each component of the flow channel structure 100. For example, the preset flow field F0 may have the sub flow field F1 in a front-end section narrow portion 115-1 of a plurality of sub-input channels 115 in the diverging flow field region 110, may have the sub flow field F2 in the back-end diverging portion 115-2 of a plurality of sub-input channels 115 in the diverging flow field region 110, may have the sub flow field F3 in the main flow channel 120, and may have the sub flow field F4 in the converging main flow channel 130. Thus, since the amount of the fluid 40 going through the flow channel structure 100 per unit of time is constant, flow fields of different flow velocities may be obtained by changing the cross-section area that the fluid 40 passes through in different structures. According to a preferred embodiment of the present disclosure, in order to keep the characteristics of microfluid, it is preferred that the channel height of the flow channel structure 100 be kept approximately constant, and flow fields of different flow velocities may be obtained by changing the channel width when the channel height in the flow channel structure 100 is kept constant.

For example, in the diverging flow field region 110, firstly it is difficult for sperm in the semen 50 to withstand the sub flow field F1 of the narrow portion 115-1 in the front-end section of the plurality of sub-input channels 115, and sperm are transported to the back-end section of the plurality of sub-input channels 115. Then, at the back-end section of the plurality of sub-input channels 115 in which the channel width is widened (for example, from the channel width W1 to the channel width W2), since the fluid flows through the gradually enlarged cross-section area, the flow velocity of the sub flow field F2 in the back-end diverging portion 115-2 of the plurality of sub-input channels 115 gradually becomes slow with respect to the sub flow field F1, and sperm in the semen 50 might gradually be able to resist the sub flow field F2. Or, after being guided to the main flow channel 120, since the main flow channel 120 significantly widens to the constant channel width W3 and is kept at the constant channel width W3, sperm in the semen 50 might be able to counter the sub flow field F3 in the main flow channel 120. Therefore, relatively active sperm may be able to counter the preset flow field F0 at the junction of the plurality of sub-input channels 115 and the main flow channel 120 or after entering the main flow channel 12 and moving along the reverse direction D2 from the second side end 14 toward the first side end 12.

Then, in the step S20, the predetermined amount of the semen 50 is injected all at once, and in the step S30, one waits a predetermined amount of time for sperm in the semen 50 to be screened by the preset flow field F0. Therefore, after the predetermined amount of time, relatively active sperm in the semen 50 may counter the sub flow field of each portion of the flow channel structure 100 and stay in the portion. For example (please refer to FIG. 4C), within the predetermined amount of time, the sperm S2 in the semen 50 might counter flow to reach a counterbalance with the sub flow field F3, and move to the junction of the sub-input channels 115 and the main flow channel 120 along the reverse direction D2, then reach a counterbalance with the sub flow field F2 here and approximately stay here. In addition, there are also some sperms S3 which, even though having no ability to counter flow, may reach a counterbalance with the sub flow field F3 so as to approximately stay in the main flow channel 120. Furthermore, the sperm S4 which have relatively low or no mobility or are even dead, the sperm fragments S4', or the sperm S5 which, even though active, are deformed (such as having a large head, multiple heads, a crooked head or a curly tail) and difficult to move forward in a straight line to counter the shearing force of the fluid 40, or those that have low linear mobility and are difficult to move forward in a straight line to counter the shearing force of the fluid 40, will be guided along the preset flow field F0 to deviate from the first side end 12. The sperm S4 or their fragments S4' or the sperm S5, after being guided to the converging main flow field 130, might be further accelerated and guided to the waste fluid outlet 310 to be discharged automatically due to the narrowing channel width of the converging main flow field 130, which accelerates the flow velocity of the sub flow field F4. That is, a portion of inactive sperm in the semen 50 may be transported to the waste fluid outlet 310 through the preset flow field F0.

Here, the scales and ratios of the sperm and the flow channel structure 100 are amplified for the purpose of clarification, and they don't represent the actual scales and ratios of sperm and the flow channel structure 100. In addition, for better understanding, relatively active sperm are illustrated with black heads, and relatively inactive sperm are illustrated with white heads.

According to some embodiments of the present disclosure, the main flow channel 120 having the approximately fixed channel width W3 may be treated as a speed down buffer region for swimming back so as to make the active sperm have sufficient time and/or space to swim back so that they can be separated from the waste fluid (dead sperm, cell fragments, inactive sperm, for example) as much as possible.

As mentioned above (please refer to FIG. 3 and FIG. 4D), after waiting the predetermined amount of time for each sperm to arrive at an approximate location of counterbalance, the step S40 of extracting the screened semen 60 may be conducted. Wherein, the screened semen 60 includes relatively active sperm originally in the semen 50. In particular, an extraction external force (for example, by the syringe pump 30) may be applied through the semen extraction port 250 to extract the screened semen 60, including the expected and required sperm and the fluid 40, to collect relatively active sperm (such as the sperm S2 and/or S3), which have stayed in the front-end section of the flow channel structure 100. In other words, the screened semen 60 includes sperm which have reached a counterbalance between their swimming speed and the flow velocity of the preset flow field F0 in a predetermined range from the first side end 12 of the flow channel structure 100.

According to some embodiments of the present disclosure, the predetermined range for collecting sperm preferably includes at least the end portions of the plurality of sub-input channels 115 communicated with the main flow channel 120 (for example, the diverging portion 115-2). For example, according to some embodiments (please refer to FIG. 4D), sperm in a first predetermined range R1 from the first side end 12 to at least portion of the front end of the main flow channel 120 may be collected. Thus, the sperm S2, those reaching a counterbalance with the sub flow field F3, and even those reaching a counterbalance with the sub flow field F2 and swimming back to the plurality of sub-input channels 115, may be collected. However, the above are merely examples, and the present disclosure is not limited thereto. For example, it is also possible to collect sperm located between the first side end 12 and the center of the main flow channel 120. Thus, the sperms S2, which reach a counterbalance with the sub flow field F3 and swim back to the plurality of sub-input channels 115, and the sperms S3, which at least reach a counterbalance with the sub flow field F3, may be collected mainly. In addition, in various embodiments, since relatively active sperm might swim back to the plurality of sub-input channels 115, and sperm can't go forward and are stuck to the end portion of the plurality of sub-input channels 115 (for example the diverging portion 115-2) due to the sub flow field F2 being strengthened by the narrowing channel width, therefore the main areas in which relatively active sperm may be collected might concentrate at the end portion of the plurality of sub-input channels 115 communicated with the main flow channel 120 (for example the diverging portion 115-2).

According to some embodiments, various characteristics (such as linearity and wobble) of each of the sperm in the semen are researched by using the technology CASA (Computer Assisted Semen Analysis) before and after sorting so as to respectively calculate the mobilities and swimming speeds of each of the collected sperm. For example, sperm before and after sorting (for example, sperm in the semen 50 and the screened semen 60) may be suctioned out to be disposed on a cytometer, and recorded in a video by a microscope, then the video is analyzed by an image processing program and a computer-assisted analysis so as to calculate various properties of sperms.

Figure 5:
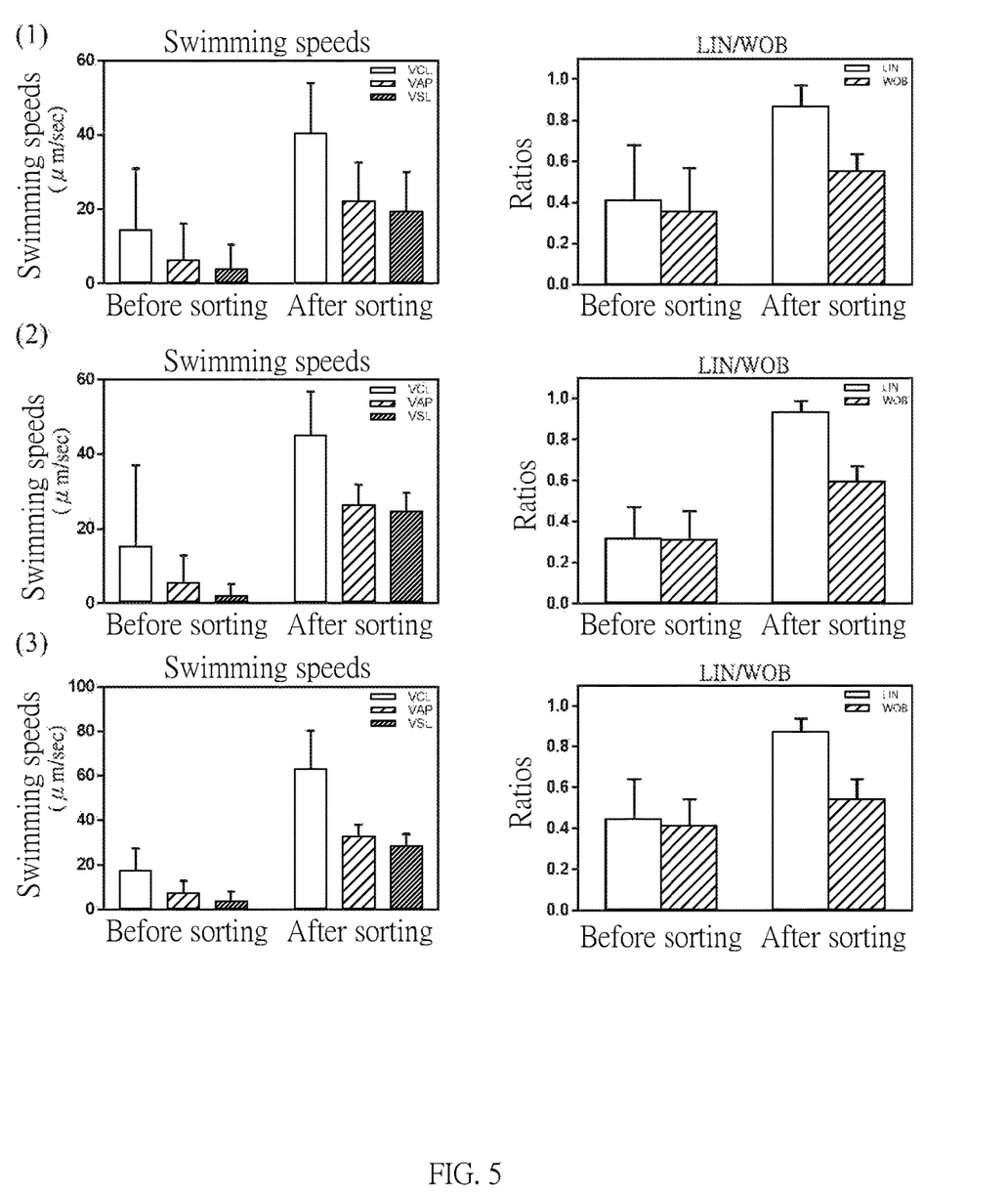
FIG. 5 is a histogram comparing qualities of sperm from different test samples before and after sorting sperm using the sperm sorting chip in an embodiment of the present disclosure.

According to some embodiments of the present disclosure, sperm collected by the sperm sorting chip 10 may have high linearity (>0.9) and be relatively active (~99%). For example, please refer to FIG. 5, which illustrates histograms to compare properties of sperm of different objects (human males (1)(2)(3) from top to bottom) before and after sorting using the sperm sorting chip 10. As such, it seems that sperm having relatively high velocity curvilinear (VCL), high velocity average path (VAP), velocity straight line (VSL), linearity (LIN), and high wobble (WOB) may be extracted from the semen after being screened by the sperm sorting chip 10.

Please continue to refer to FIG. 3. After the step S40 is completed, the method 20 for sorting sperm may further include repeating the step S20 to the step S40 one or more times. That is, another lot of the semen 50 may be injected to wait the predetermined amount of time for the semen to be screened, and the screened semen 60 may be collected so that different lots of the semen 50 may be screened. In particular, since the sperm sorting chip 10 according to the present disclosure includes the semen extraction port 250 and the waste fluid outlet 310 separated from each other and located at opposite two side ends (for example, the first side end 12 and the second side end 14 which are opposite to each other), it is possible to decrease or avoid the problem of mix-up (for example, through the same port, waste fluids at back-end section is discharged at first, and then the screened semen 60 flowed to the back-end section after the waste fluid is extracted and collected) which may happen when discharging waste fluids and collecting screened semen 60 from the same port (for example, a port corresponding to the location of the waste fluid outlet 310). Therefore, according to each embodiment of the present disclosure, processes of screening and collecting may be repeated one or more times so as to decrease or avoid the problem of mixing the waste fluid and the screened semen 60.

In addition, since the waste fluid outlet 310 is located at a different side end from the semen extraction port 250, screening and collecting may also cost less time. In particular, since the screened semen 60 may be collected without waiting for the complete discharge of the waste fluids from a same port so as to decrease the screening time with respect to the condition of discharging waste fluids and collecting the screened semen 60 from a same port.

Furthermore, since the screened semen 60 is extracted by applying an extraction external force through the semen extraction port 250 located at the first side end 12, it is also possible to decrease or avoid the situation of carelessly collecting sperm with poor quality that are stuck or remained at the back-end section and not discharged from the waste fluid outlet 310 of the second side end 14. Thus, it is possible to avoid mixing the sorted sperm and waste fluids or the unsorted sperms, resulting in poor sorting effectiveness.

As mentioned above, since the waste fluid outlet 310 and the semen extraction port 250 are located at different side ends, the sperm sorting chip 10 and the method 20 for sorting sperm according to the each embodiment of the present disclosure may have at least one or more of the following effects and advantages: time for screening may be decreased so as to avoid or reduce the likelihood of decreasing the mobility of sperm; the sorted sperm are relatively less likely to be mixed with waste fluids (which might contain sperm of poor quality); microfluid system whose flux is small may process larger amount of specimen at the same time; and the same chip may conduct the process of screening and collecting many times and not only one time.

In addition, according to some embodiments of the present disclosure, one or more of the fluid injection port 210, the semen injection port 220, the semen extraction port 250, and the waste fluid outlet 310 may be selectively closed (for example, by a valve) in order to reduce or avoid sperm or fluids overflowing or being backwashed from wrong ports during input or output. For example, the semen extraction port 250 may be closed when injecting the semen 50 in the step S20 so as to avoid the injected semen 50 overflowing from the semen extraction port 250. Similarly, the semen injection port 220 may be closed when extracting the screened semen 60 in the step S40 so as to avoid the screened semen 60 overflowing from the semen injection port 220 when extracting the screened semen 60. Furthermore, according to some embodiments of the present disclosure, the semen injection port 220 and the fluid injection port 210 may also be closed at the same time when extracting the screened semen 60 in the step S40 so as to avoid the screened semen 60 overflowing from the semen injection port 220 or the fluid injection port 210 or to avoid stress generated by the fluid injection port 210 continuously injecting the fluid 40 and preventing the screened semen 60 from being extracted, or to avoid the extracted screened semen 60 being further diluted by the fluid 40 continuously injected through the fluid injection port 210 when extracting the screened semen 60. However, the patterns of selectively opening or closing each port are merely examples, and the present disclosure is not limited thereto.

In addition to the aforementioned situations of especially closing the fluid injection port 210, the fluid 40 may be continuously injected through the fluid injection port 210 so as to maintain the preset flow field F0 after the preset flow field F0 is established in the step S10 in the overall sperm sorting method 20. For example, the aforementioned preset flow field F0 may be generated based on gravity by continuously injecting the fluid 40 with a height difference. However, methods for continuously injecting the fluid to generate the preset flow field F0 are not limited thereto. For example, the preset flow field F0 may also be generated by continuously inputting the fluid 40 using a syringe pump.

In summary, according to each of the embodiments of the present disclosure, sperm with relatively high quality (for example, relatively active sperm or sperm with relatively good morphology) may be sorted by the sperm sorting chip 10 whose structure is relatively simple and the method 20 for sorting sperm and using the same. Therefore, the sorted sperm, for example, may be used for in vitro fertilization or internal fertilization so as to enhance opportunities for succeeding artificial insemination or to improve health status of fertilized eggs. Thus, the sperm sorting chip 10 according to each of the embodiments of the present disclosure and the method 20 for sorting sperm using the same may contribute to the technical field of artificial reproduction or the field of biomedicine.

The aforementioned descriptions merely represent some exemplary embodiments of the present disclosure. It should be noted that various alternations and modification without departing from conception principle of the present disclosure are all viewed as the present disclosure. It is clear for people skilled in the art that the scope of the present disclosure are determined by claims and various alternations such as replacements, combinations, modifications, and diversions are all consequently viewed as being embraced by the scope of the present disclosure determined by claims without departing from the conception principle of the present disclosure.

What is claimed is:

1. A sperm sorting chip comprising:
 a flow channel structure sequentially configured with a diverging flow field region, a main flow channel, and a converging main flow channel intercommunicated with each other from a first side end to a second side end, wherein the first side end is opposite to the second side end;
 a fluid injection port, a semen injection port, and a semen extraction port separately located at the first side end and communicated with a main input channel of the diverging flow field region; and
 a waste fluid outlet located at the second side end and communicated with the converging main flow channel,
 wherein the diverging flow field region further includes a plurality of sub-input channels derived from the main input channel and converged to the main flow channel, and the plurality of sub-input channels have a diverging channel, which has a sector area at the intersection with the main flow channel, and
 wherein the converging main flow channel has a converging channel width toward the waste fluid outlet;
 wherein the fluid injection port is located above, in a direction of gravity with respect to the diverging flow field region, the main flow channel, the converging main flow channel or a combination thereof.

2. The sperm sorting chip according to claim 1, wherein the diverging flow field region is configured to form a tree branch from an end of the main input channel away from the first side end as a starting node toward the second side end, and
 wherein the plurality of sub-input channels are configured to form the tree branch based on the starting node or have one or more tree branch sub-channels of different tiers from the starting node.

3. The sperm sorting chip according to claim 1, wherein a sum of the largest widths of each of the plurality of sub-input channels is smaller than or equal to a width of the main flow channel.

4. The sperm sorting chip according to claim 1, wherein one or more of the fluid injection port, the semen injection port, and the semen extraction port are selectively opened or closed.

5. A method for sorting sperm using the sperm sorting chip according to claim 1, comprising:
 a step (a): injecting a fluid through the fluid injection port, and keeping the fluid entering the flow channel structure continuously to establish a preset flow field;
 a step (b): injecting a predetermined amount of semen to the main input channel through the semen injection port;

a step (c): waiting a predetermined amount of time for the semen to be screened by the preset flow field; and a step (d): applying an extraction external force through the semen extraction port to extract the screened semen;

wherein the semen extraction port is at an opposite side to a place where waste fluid flows out of the sperm sorting chip;

wherein relatively inactive sperms in the semen is transported to the waste fluid outlet by the preset flow field, and the screened semen includes relatively active sperms in the semen;

wherein the preset flow field is generated based on gravity by injecting the fluid from a place higher than the sperm sorting chip.

6. The method according to claim 5, wherein the screened semen includes sperms whose swimming speed reach a balance with a flow velocity of the preset flow field in a predetermined range from the first side end of the flow channel structure.

7. The method according to claim 6, wherein the predetermined range at least includes end portions of the plurality of sub-input channels communicated with the main flow channel.

8. The method according to claim 5, wherein the fluid is mHTF or sperm culture media.

9. The method according to claim 5, wherein after the step (d) is completed, the method further includes repeating the step (b) to the step (d) one or more times.

10. The method according to claim 5, further comprising:

closing the semen extraction port in the step (b), and closing the semen injection port in the step (d).

11. The method according to claim 10, further comprising:

closing the semen injection port and the fluid injection port at the same time in the step (d).

* * * * *